United States Patent [19]

Atalar et al.

[11] Patent Number: 4,663,745
[45] Date of Patent: May 5, 1987

[54] CIRCUIT ARRANGEMENT FOR SEPARATING HIGH-FREQUENCY PULSES GENERATED BY AN ACOUSTIC REFLECTING LENS ARRANGEMENT

[75] Inventors: Abdullah Atalar, Ankara, Turkey; Herbert Fischbach, Wetzlar, Fed. Rep. of Germany

[73] Assignee: Ernst Leitz Wetzlar GmbH, Wetzlar, Fed. Rep. of Germany

[21] Appl. No.: 712,109

[22] Filed: Mar. 15, 1985

[30] Foreign Application Priority Data

Mar. 17, 1984 [DE] Fed. Rep. of Germany ....... 3409930

[51] Int. Cl.$^4$ ............................................. G01S 15/89
[52] U.S. Cl. ....................................... 367/87; 73/629; 367/903
[58] Field of Search ........................... 367/87, 99, 903; 73/629, 632

[56] References Cited

U.S. PATENT DOCUMENTS

| | | | |
|---|---|---|---|
| 3,296,589 | 1/1967 | Ikrath | 367/903 |
| 3,475,700 | 10/1969 | Ertel | 333/7 |
| 4,078,217 | 3/1978 | Beno | 333/97 S |
| 4,127,830 | 11/1978 | Chalifour et al. | 333/7 D |
| 4,523,472 | 6/1985 | Blades | 73/632 |

FOREIGN PATENT DOCUMENTS 0032732 7/1981 European Pat. Off. .
0039457 11/1981 European Pat. Off. .

OTHER PUBLICATIONS

J. Heiserman et al, "Cryogenic Acoustic Microscopy", J. Acoust. Soc. Am., 67(5), May 1980, pp. 1529-1637.
Y. Guanggi et al, "Pulse-Compression Subsurface Acoustic Microscopy", Electronics Letters, vol. 18, No. 18, Sep. 2, 1982, pp. 767-769.
J. Attal, "Signal Processing in the Reflective Acoustic Microscope", Electronics Letters, vol. 14, No. 14, Jul. 20, 1978, pp. 472-473.
Nongaillard et al, "Visualization of Thick Specimens Using a Reflection Acoustic Microscope", J. Appl. Phys., 50(3), Mar. 1979, pp. 1245-1249.

Primary Examiner—Richard A. Farley
Attorney, Agent, or Firm—Schwartz, Jeffery, Schwaab, Mack, Blumenthal & Evans

[57] ABSTRACT

A circuit arrangement for separating high-frequency pulses produced successively in time at a piezoelectric transducer of an acoustic reflection lens arrangement. According to the invention, the transducer is preceded by a three-way pin switch, the common end of the wiper of which is connected to the acoustic lens, the other end of the wiper being alternately connected in a first position to the output of a transducer oscillator, in a second position to a 50-Ohm resistor, or in a third position to a measurement circuit.

17 Claims, 1 Drawing Figure

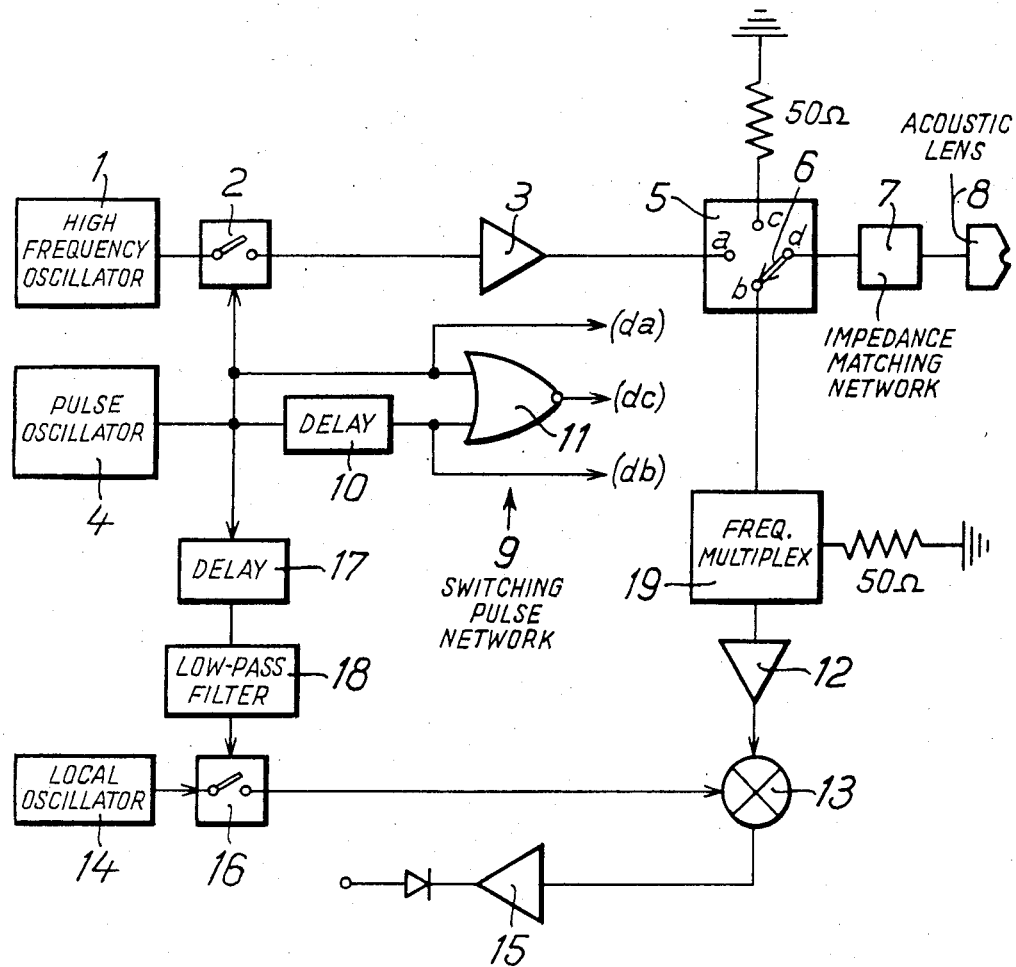

CIRCUIT ARRANGEMENT FOR SEPARATING HIGH-FREQUENCY PULSES GENERATED BY AN ACOUSTIC REFLECTING LENS ARRANGEMENT

BACKGROUND OF THE INVENTION

This invention relates to a circuit arrangement for separating high-frequency pulses generated successively in time by a piezoelectric transducer of an acoustic reflecting lens arrangement.

Acoustical microscopy can be carried out within a frequency range of from 50 to 5,000 MHz. In acoustical reflection microscopy, short pulses of this frequency having a duration of about 10-100 nsec and a pulse repetition frequency of about 500 kHz are used.

The most important component of the acoustical microscope is the acoustic lens arrangement. This generally comprises a peizoelectric transducer which converts electric energy into acoustic energy and back again, and a lens surface in the form of a spherical cavity in the surface of the acoustic transmission medium opposite to the transducer. The acoustic transmission medium is selected to have a high sound velocity in order to reduce spherical aberrations when the acoustic lens is coupled to a liquid transition medium. Sapphire is normally used as transmission medium and distilled water as coupling means.

The piezoelectric transducer can be optimized for a predetermined frequency range, but its bandwidth will not exceed one or two octaves. This means that the acoustic lens arrangement must be exchanged if it is intended to change the required operating frequency. It is desirable, however, that the electronic circuit driving the acoustic lens arrangement in the form of short pulses and receiving the echo pulses from the object can be kept unchanged. This is because the amount spent on the circuitry for an acoustic lens arrangement is a significant factor in the overall system cost.

The necessary electronic circuitry is also complicated because the internal reflections in the acoustic transmission medium are rather large and the echo pulses from the object, which are the actual item of interest, are relatively small due to the high attenuation in the liquid coupling medium. For this reason, it is necessary to insert between the output of the circuit generating the excitation pulses, the input of the circuit used for processing the measurement signal, and the transducer of the acoustic lens arrangement, an interface which separates the high-frequency pulses occurring successively in time so that all three electronic components can be considered as being largely decoupled from each other.

A simple circuit element which, however, only incompletely solves this problem, is a microwave circulator which, in a first phase, guides the excitation pulse to the transducer, then blocks the entrance and opens the conduction path from the transducer to the measurement signal processing circuit. It must be noted that such a circulator does not allow complete line isolation. Thus, a not negligible portion of the excitation pulse always passes directly to the measurement signal line. On this leakage signal, electric reflections are superimposed which are produced by a mismatch between the characteristic impedances of the feeder to the transducer and of the transducer itself. This signal, which is generated first in time, shall be designated by A.

Despite anti-reflection coating of the boundary area, a second signal B is produced by internal reflection of the excitation pulse at the boundary area between the acoustic transmission medium and the liquid coupling medium. This second signal is typically 10-20 dB smaller than pulse A and is delayed with respect to this pulse by a time $t_1$ which is determined by the velocity of propagation in the acoustic medium and the length of the transmission path.

A signal C representing the pulse reflected at the object follows with a further time delay $t_2$. Its magnitude is considerably smaller than all other signals because of attenuation in the liquid coupling medium. Its amplitude is determined by the shape of the lens since this determines the transmission path in the liquid, by the operating frequency, and by the attenuation parameters of the liquid. The amplitude of signal C is typically 30-90 dB lower than that of signal A.

Internal reflection inside the lens body can also produce a signal D which has a time delay $t_1$ with respect to signal B.

Since the circulator is incapable of separating the signals A, B, C, and D, difficulties arise in isolating the signal C, the only signal which is actually of interest. Also, the amplifiers available in practice have a long post-saturation recovery time. As a rule, the linearity of the amplifiers has not yet been restored when signal C arrives since signal B is considerably larger than signal C and the latter follows the former very rapidly.

Another very important problem arises as a result of the abovementioned mismatch of the impedances on the feeder to the transducer. Every signal entering this conduction path tends to be reflected back and forth for a long time. For constructional reasons, the length of this feeder cannot be made arbitrarily small. This is why the duration of the electric reflections on this line can be as long as a time interval $t_2$ sufficient to cause undesirable problems of interference with the object signal C.

From Electronics Let., Vol. 14 (1978), pp. 472-473, a circuit arrangement is known which is intended to be used for suppressing the leakage signal from the circulator and interfering echo signals from the acoustic lens arrangement. For this purpose, a switch is inserted into the measurement signal input behind the circulator, which switch is opened only after a time corresponding to the time of transit of the excitation pulse to the specimen and back to the switch. Pin switches are suitable switches for such purposes. For the proposed system, a very clean and thus expensive switch with a minimum of switching spikes must be selected since otherwise a following amplifier would be overdriven by the switching spikes, which contain very high frequency components. The system has the further disadvantage that it is virtually impossible to eliminate the previously-mentioned reflections on the feeder to the transducer. In addition, the possible frequency range for the excitation pulses and thus the working frequencies for the acousto-microscopic examination, which range can be covered by exchanging the acoustic lens system, is limited by the characteristics of the circulator.

From J. Appl. Phys. Vol. 50 (1979), pp. 1245-1249, a circuit arrangement is known in which the circulator is replaced by a hybrid coupler. Such a coupler is a passive component in which electric signals can propagate only in predetermined directions. The attenuation in the directional conductors is relatively large. The signal losses are about 6 dB. Capacitive coupling between individual directional conductors frequently results in signal crosstalk.

The known hybrid coupler is arranged in such a way that a direct passage exists between the high-frequency generator and the transducer of the acoustic lens arrangement, and a further directional conductor from the transducer to the measurement signal processing circuit. A switch controlled with time delay is again inserted into this line so that the interfering echo signals can be suppressed. From the hybrid coupler input another directional conductor extends which is terminated by a 50-Ohm resistor. This makes it possible to attenuate reflections produced by mismatch on the line from the high-frequency generator to the hybrid coupler. Here, too, the problem of the reflections on the line from the transducer to the measurement signal input switch and of suppression of the switching spikes of this switch has not been solved.

Another circuit arrangement for suppressing the undesirable echo signals is specified in European Pat. No. 0.032,732. The solution proposed in that patent consists in arranging a second acoustic lens next to the acoustic lens arrangement used for object scanning, the second acoustic lens having the same constructional data and a reference object. Subtraction of the two signal sequences returning from the lenses is intended to leave only the cleaned-up measurement signal. Because of the second lens arrangement, this arrangement is very expensive and presents great difficulties in implementing identical lens parameters.

SUMMARY OF THE INVENTION

For this reason, the present invention has the basic object of providing a circuit arrangement which makes it possible, with low expenditure for components, to decouple the working phases of excitation of the acoustic lens arrangement, to suppress the interfering signals, and to pass on the measurement signal electrically from one system element to the next. Another object of the present invention is to make it possible to achieve simultaneously an improvement in the quality of the measurement signal.

In a circuit arrangement according to the present invention, this object is achieved through provision of a circuit for separating high-frequency pulses generated successively in time in an acoustic reflecting lens arrangement, including an acoustic lens for generating acoustic signals, for receiving reflected components of the generated acoustic signals, and for generating a measurement pulse corresponding to the reflected components, a transducer oscillator for generating an excitation pulse to drive the acoustic lens to generate the acoustic signals, and a measurement circuit for measuring the measurement pulse, the circuit comprising a three-way pin switch having a wiper, the common end of the wiper being connected to the acoustic lens and the other end of the wiper being selectably and alternately connectible with the transducer oscillator in a first position, a resistive load in a second position, or the measurement circuit in a third position.

BRIEF DESCRIPTION OF THE DRAWING

Other features of the present invention will be more clearly understood from the following description read in conjunction with the drawing, which is a schematic diagram of a circuit according to the present invention.

DETAILED DESCRIPTION OF PREFERRED EMBODIMENTS

A high-frequency oscillator 1 oscillates at the working frequency required for acousto-microscopic examination. A pin switch 2 is used to generate short excitation pulses which are amplified in a following power amplifier 3. The pin switch 2 is clocked by a pulse oscillator 4. The excitation pulses are fed to the input "a" of a three-way pin switch 5. The end "d" of the wiper 6 is connected via an impedance matching network 7 to a piezoelectric transducer, not shown in greater detail, of an acoustic lens arrangement 8. The output "b" of the switch 5 is connected to the measurement circuit in a manner which will be described below, and the output "c" is connected to ground potential via a 50-Ohm resistor.

The switching positions of the three-way pin switch 5 are activated via a switching pulse network 9. The clock pulse controlling the pin switch 2 also establishes the connection (da). Connection (db) is established by means of a clock pulse delayed in a delay section 10 by the transit time of the measurement pulse. These switching positions are maintained only for the duration of the clock pulse. At all other times, in which neither the clock pulse nor the delayed clock pulse are present at the NOR gate 11, this gate drives the wiper 6 into position (dc).

The three-way pin switch 5 brings the following advantages in the circuit arrangement:

(a) A pin switch has a typical bandwidth of about 100–4,000 MHz. For this reason, it is a very good replacement for many circulators if it is intended to cover a very large frequency range with the excitation and measurement circuit. In contrast, a microwave circulator has a typical bandwidth of only about one octave.

(b) In order to generate the high excitation pulse on/off ratio necessary for operating the system, normally two pin switches 2 are connected in series, each of which has an on/off ratio of 60–80 dB. The three-way pin switch 5 additionally replaces one of these pin switches.

(c) In switch position (dc), the feeder to the transducer of the acoustic lens arrangement is terminated by a 50-Ohm resistor. This very effectively attenuates the echo pulse reflections produced on this line which can be separated especially also from the line to the measurement circuit and cannot produce any interference problems in this area.

(d) The three-way pin switch operates at very low losses. Since the switching states are electrically completely insulated from each other, no leakage signals will be produced on the respective other lines.

One disadvantage of the three-way pin switch consists in that it generates switching pulses during the switching times. In the worst case, the amplitudes of these switching spikes can become very large and the frequency components contained in them can reach very high frequencies. This applies especially if a very fast pin switch is used. The switching spikes are then considerably amplified by the receiving system and can quite easily reach amplitudes of the order of magnitude of the object pulses, thus creating new interference problems.

This disadvantage can be countered by incorporating a superheterodyne circuit in the measuring circuit, consisting of a preamplifier 12, a mixer 13, a local oscillator 14, and an intermediate frequency amplifier 15. At a predetermined working frequency of the acoustic microscope, the local oscillator frequency is tuned in such a way that the difference frequency after mixing in mixer 13 is equal to the intermediate frequency of the intermediate-frequency amplifier 15. An intermediate-frequency amplifier has only a very limited gain at all frequencies deviating from the intermediate frequency. For this reason, its output becomes nearly zero if the local oscillator is damped.

In the exemplary circuit shown, the local oscillator 14 is only switched on, via a pin switch 16, during the time in which the measurement signal arrives from the object. Thus, this method is especially effective when the switching pulses of the three-way pin switch 5 are actually interfering with the signal evaluation. The three-way pin switch 5 is switched on before the local oscillator 14 is switched and it is switched off after the local oscillator has been switched off. In this way, the switching spikes generated by the three-way pin switch are not present, or at least very greatly reduced, at the output of the intermediate-frequency amplifier 15. The switching sequence required for the local oscillator 14 is achieved by appropriate delay of the clock pulse, generated by the pulse oscillator 4, in a delay section 17, and following low-pass filter 18, the last of which also flattens the steepness of the switching edges for the pin switch 16.

A further improvement of the signal processing process can be achieved by connecting a frequency multiplexer 19 in front of the measurement circuit. Frequency multiplexer 19 is selected in such a way that it divides the input signal into two frequency ranges. The low-frequency output of the multiplexer is terminated by a 50-Ohm resistor and the high-frequency output is connected to the preamplifier 12. This arrangement ensures that the prodominant, low-frequency component in the switching pulses of the three-way pin switch 5 passes to the 50-Ohm resistor rather than to the input of the preamplifier 12.

What is claimed is:

1. A circuit for separating high-frequency pulses generated successively in time in an acoustic lens arrangement including an acoustic lens for generating acoustic signals, for receiving reflected components of said generating acoustic signals, and for generating a measurement pulse corresponding to said reflected components, a transducer oscillator for generating an excitation pulse to drive said acoustic lens to generate said acoustic signals, and a measurement circuit for measuring said measurement pulse, comprising a three-way pin switch having a wiper, the common end of said wiper being connected to said acoustic lens, and the other end of said wiper being alternately connectible with said transducer oscillator in a first position, a first resistive load in a second position, or said measurement circuit in a third position.

2. A circuit as claimed in claim 1, further comprising a frequency multiplexer interposed between said other end of said wiper in said third position and said measurement circuit, said frequency multiplexer having an input connected to said wiper in said third position, a high-frequency output connected to said measurement circuit, and a low frequency output connected to a second resistive load.

3. A circuit as claimed in claim 2, further comprising a control circuit connected to said three-way pin switch, and adapted to connect said wiper in said first position for the duration of said excitation pulse, in said third position for the duration of said measurement pulse, and otherwise in said second position.

4. A circuit as claimed in claim 3, wherein said measuring circuit further comprises a superheterodyne receiver circuit comprising:
a switched local oscillator;
a mixer; and
an intermediate-frequency amplifier;
said circuit further comprising a switch pulse-forming circuit adapted to damp the local oscillator at least during switching of said wiper in said three-way pin switch between the second and third positions of said wiper.

5. A circuit as claimed in claim 1, wherein said resistive load comprises a 50-Ohm resistor connected at one end to said wiper in said second position, and at its other end to ground.

6. A circuit as claimed in claim 3, wherein said first resistive load comprises a 50-Ohm resistor connected at one end to said wiper in said second position, and at its other end to ground.

7. A circuit as claimed in claim 2, wherein said first resistive load comprises a 50-Ohm resistor connected at one end to said wiper in said second position, and at its other end to ground.

8. A circuit as claimed in claim 2, wherein said measuring circuit comprises a superheterodyne receiver circuit comprising:
a switched local oscillator;
a mixer; and
an intermediate-frequency amplifier;
said circuit further comprising a switch pulse-forming circuit adapted to damp the local oscillator at least during switching of said wiper in said three-way pin switch between the second and third positions of said wiper.

9. A circuit as claimed in claim 8, wherein said first resistive load comprises a 50-Ohm resistor connected at one end to said wiper in said second position, and at its other end to ground.

10. A circuit as claimed in claim 1, further comprising a control circuit connected to said three-way pin switch, and adapted to connect said wiper in said first position for the duration of said excitation pulse, in said third position for the duration of said measurement pulse, and otherwise in said second position.

11. A circuit as claimed in claim 10, wherein said measuring circuit further comprises a superheterodyne reciever circuit comprising:
a switched local oscillator;
a mixer; and
an intermediate-frequency amplifier;
said circuit further comprising a switch pulse-forming circuit adapted to damp the local oscillator at least during switching of said wiper in said three-way pin switch between the second and third positions of said wiper.

12. A circuit as claimed in claim 11, wherein said resistive load comprises a 50-Ohm resistor connected at one end to said wiper in said second position, and at its other end to ground.

13. A circuit as claimed in claim 10, wherein said resistive load comprises a 50-Ohm resistor connected at one end to said wiper in said second position, and at its other end to ground.

14. A circuit as claimed in claim 1, wherein said measuring circuit comprises a superheterodyne receiver circuit comprising:

a switched local oscillator;
a mixer; and
an intermediate-frequency amplifier;
said circuit further comprising a switch pulse-forming circuit adapted to damp the local oscillator at least during switching of said wiper in said three-way pin switch between the second and third positions of said wiper.

15. A circuit as claimed in claim 14, wherein said resistive load comprises a 50-Ohm resistor connected at one end to said wiper in said second position, and at its other end to ground.

16. An acoustic reflecting lens arrangement comprising:
   an acoustic lens for generating acoustic signals, for receiving reflected components of said generated acoustic signals, and for generating a measurement pulse corresponding to said reflected components;
   a transducer oscillator for generating an excitation pulse to drive said acoustic lens to generate said acoustic signals;
   a measurement circuit for measuring said measurement pulse; and
   a three-way pin switch having a wiper, the common end of said wiper being connected to said acoustic lens, and the other end of said wiper being alternately connectible with said transducer oscillator in a first position, a resistive load in a second position, or said measurement circuit in a third position.

17. An acoustic reflecting lens arrangement comprising:
   an acoustic lens for generating acoustic signals, for receiving reflected components of said generated acoustic signals, and for generating a measurement pulse corresponding to said reflected components;
   a transducer oscillator for generating an excitation pulse to drive said acoustic lens to generate said acoustic signals;
   a frequency multiplexer heading a low-frequency output connected to ground through a resistive load, and a high-frequency output;
   a measurement circuit comprising a preamplifier connected to the high-frequency output of said frequency mutliplexer, a mixing circuit having one input connected to said preamplifier, a local oscillator switchably connected to a second input of said mixing circuit, and an intermediate amplifier connected to the output of said mixing circuit;
   means for switchably connecting said local oscillator to said mixing circuit; and
   a three-way pin switch having a wiper, the common end of said wiper being connected to said acoustic lens, and the other end of said wiper being alternately connectible with said transducer oscillator in the first position, a resistive load in a second position, or said frequency multiplexer in a third position.

* * * * *